(12) United States Patent
Cottrell et al.

(10) Patent No.: US 6,407,255 B2
(45) Date of Patent: Jun. 18, 2002

(54) CHEMICAL SYNTHESIS OF 1,2,4-TRIAZOLINONE DERIVATIVE

(75) Inventors: Ian Frank Cottrell, Hertford (GB); Ulf H Dolling, Westfield, NJ (US); David Hands; Robert Darrin Wilson, both of London (GB)

(73) Assignee: Merck Sharp & Dohme Ltd., Hoddesdon (GB)

( * ) Notice: Subject to any disclaimer, the term of this patent is extended or adjusted under 35 U.S.C. 154(b) by 0 days.

(21) Appl. No.: 09/950,286

(22) Filed: Sep. 10, 2001

Related U.S. Application Data

(62) Division of application No. 09/719,712, filed as application No. PCT/GB99/01842 on Jun. 10, 1999, now Pat. No. 6,297,376.

(30) Foreign Application Priority Data

Jun. 16, 1998 (GB) ................................. 9813025

(51) Int. Cl.[7] ........................................... C07D 249/12
(52) U.S. Cl. ..................................... 548/263.2
(58) Field of Search ........................ 548/263.2

(56) References Cited

FOREIGN PATENT DOCUMENTS

| WO | WO 95/16679 | 6/1995 |
|----|-------------|--------|
| WO | WO 95/18124 | 7/1995 |
| WO | WO 95/23798 | 9/1995 |
| WO | WO 95/30674 | 11/1995 |

OTHER PUBLICATIONS

Cowden et al, *Chemical Abstracts*, vol. 134, No. 115, 901, 2000.*
Chemical Abstracts, vol.: 76, No. 7, p.: 317 (1972).
Chemical Abstracts, vol.: 71, No. 13, p.: 315 (1969).

* cited by examiner

*Primary Examiner*—Robert W. Ramsuer
(74) *Attorney, Agent, or Firm*—J. Eric Thies; David L. Rose

(57) ABSTRACT

The present invention relates to a process for the preparation of morpholine derivatives of formula (I) which are useful as a therapeutic agents.

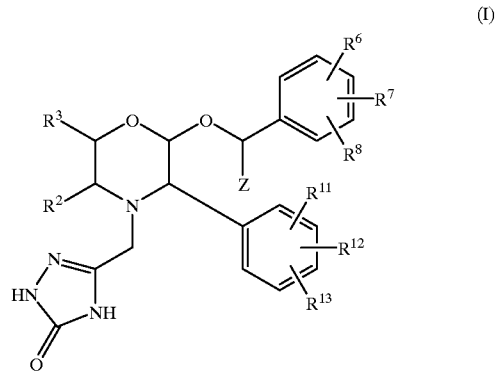

29 Claims, No Drawings

CHEMICAL SYNTHESIS OF 1,2,4-TRIAZOLINONE DERIVATIVE

CROSS REFERENCE TO RELATED APPLICATIONS

This application is a Division of Ser. No. 09/719,712, filed Dec. 15, 2000, now U.S. Pat. No. 6,297,376 which is a US National Phase application under 35 U.S.C. §371 of PCT Application No. PCT/GB99/01842, filed Jun. 10, 1999, which claims priority under 35 U.S.C. §119 from GB Application No. 9813025.5, filed Jun. 16, 1998.

The present invention relates to a process for the preparation of morpholine derivatives, and in particular, the compound 2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl)morpholine, which are useful as therapeutic agents.

Compounds of formula (I), below, which are described in International patent specification No. WO 95/16679 (published Jun. 22, 1995), are potent and selective substance P (or neurokinin-1) receptor antagonists.

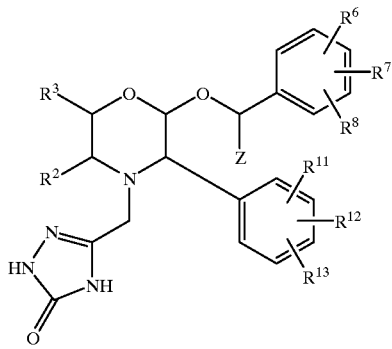

(I)

wherein
  $R^2$ and $R^3$ are independently selected from the group consisting of:
   (1) hydrogen,
   (2) $C_{1-6}$alkyl,
   (3) $C_{2-6}$alkenyl, and
   (4) phenyl;
  $R^6$, $R^7$ and $R^8$ are independently selected from the group consisting of:
   (1) hydrogen,
   (2) $C_{1-6}$alkyl,
   (3) fluoro,
   (4) chloro,
   (5) bromo,
   (6) iodo, and
   (7) —$CF_3$;
  $R^{11}$, $R^{12}$ and $R^{13}$ are independently selected from the group consisting of:
   (1) hydrogen,
   (2) $C_{1-6}$alkyl,
   (3) fluoro,
   (4) chloro,
   (5) bromo,
   (6) iodo, and
   (7) —$CF_3$; and
  Z is $C_{1-4}$alkyl.

In particular, the compound 2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl)morpholine has shown potential in the treatment of emesis, depression and anxiety. Substance P antagonists are also being investigated for other neuropsychiatric diseases, including bipolar disorder and schizophrenia, as well as postherpetic neuralgia and pain.

International patent specification No. WO 95/16679 describes the preparation of 2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl)morpholine (hereinafter referred to as Compound A), which has the structure:

Compound A

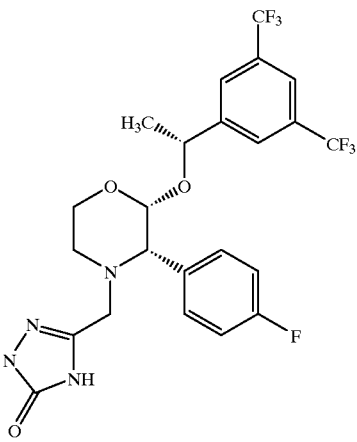

by a two-step process starting from 2-(R)-(1-(R)-(3,5-bis(trifluoromethyl)-phenyl)ethoxy)-3-(S)-(4-fluorophenyl)morpholine. With reference to Examples 70 and 75 in WO 95/16679, Compound A is prepared as follows:

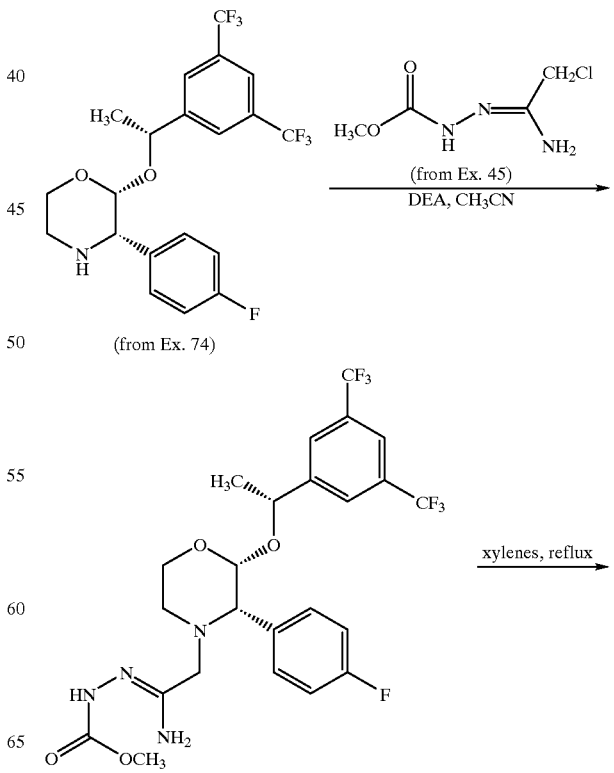

-continued

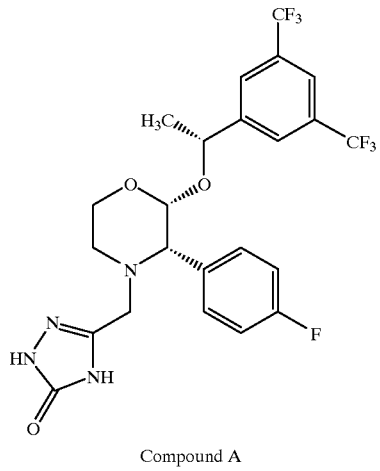

Compound A

This prior art process and in particular its requirement for a high temperature cyclisation step presents a number of practical difficulties which render it inconvenient when attempted on anything other than a relatively small scale. Therefore, there is a need for the development of a process which is readily amenable to scale-up and hence capable of practical application to the manufacturing plant.

The present invention accordingly provides a convenient, efficient process which utilizes a one-step alkylation with 3-chloromethyl-1,2,4-triazolin-5-one at ambient temperature that produces compounds of formula (I), and in particular Compound A, in a higher yield than the prior art two-step synthesis and which avoids a high temperature cyclisation. The novel process of the present invention is not only more energy efficient (since it requires no heating), but it is also more productive allowing for a shorter time-cycle on large scale and a higher operating concentration. The ability to effect the process of the present invention in one reaction vessel, in which the desired product crystallises from the reaction mixture at ambient temperature is a clear advantage over the prior art synthesis.

Thus, in a first aspect of the present invention, there is provided a process for the preparation of a compound of formula (I)

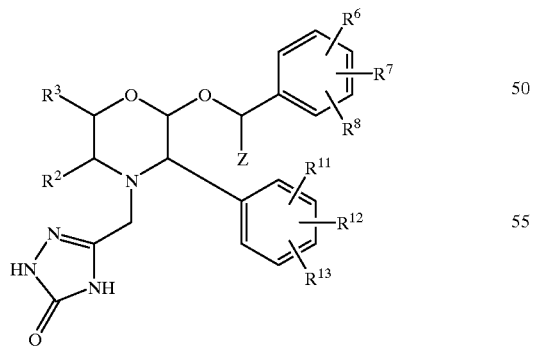

wherein

R$^2$ and R$^3$ are independently selected from the group consisting of:
(1) hydrogen,
(2) $C_{1-6}$alkyl,
(3) $C_{2-6}$alkenyl, and
(4) phenyl;

R$^6$, R$^7$ and R$^8$ are independently selected from the group consisting of:
(1) hydrogen,
(2) $C_{1-6}$alkyl,
(3) fluoro,
(4) chloro,
(5) bromo,
(6) iodo, and
(7) —CF$_3$;

R$^{11}$, R$^{12}$ and R$^{13}$ are independently selected from the group consisting of:
(1) hydrogen,
(2) $C_{1-6}$alkyl,
(3) fluoro,
(4) chloro,
(5) bromo,
(6) iodo, and
(7) —CF$_3$; and Z is $C_{1-4}$alkyl, which comprises:

(i) reacting a compound of formula (II)

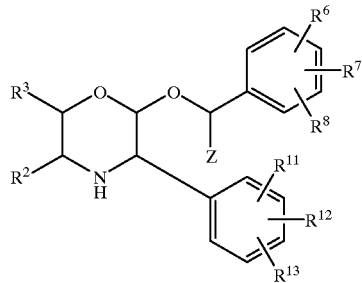

or a salt thereof, wherein R$^2$, R$^3$, R$^6$, R$^7$, R$^8$, R$^{11}$, R$^{12}$, R$^{13}$ and Z are as previously defined, with a compound of formula (III)

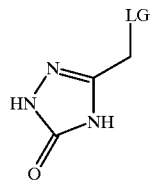

wherein LG is a leaving group selected from halogen (e.g. bromo, chloro or iodo) or an alkyl- or arylsulfonate group (e.g. mesylate or tosylate), in an organic solvent and in the presence of a base; and (ii) collecting the resultant crystalline compound of formula (I).

In a particularly preferred aspect of the present invention, there is provided a process for the preparation of the compound 2-(R)-(1-(R)-(3,5-bis(trifluoromethyl)phenyl) ethoxy)-3-(S)-(4-fluorophenyl)-4-(3-(5-oxo-1H,4H-1,2,4-triazolo)methyl)morpholine which comprises:

(i) reacting 2-(R)-(1-(R)-(3,5-bis(trifluoromethyl)phenyl) ethoxy)-3-(S)-(4-fluorophenyl)morpholine or a salt thereof, with a compound of formula (III)

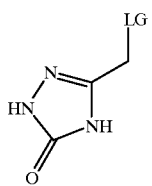

(III)

as previously defined, in an organic solvent and in the presence of a base; and (ii) collecting the resultant crystalline 2-(R)-(1-(R)-(3,5-bis(trifluoromethyl)phenyl)ethoxy)-3-(S)-(4-fluorophenyl) -4-(3-(5-oxo-1H,4H-1,2,4-triazolo)methyl)morpholine.

In the compounds of formulae (I) and (II), preferably $R^2$ and $R^3$ are both independently hydrogen.

In the compounds of formulae (I) and (II), preferably $R^6$ and $R^7$ are independently selected from fluoro and —$CF_3$. In particular. $R^6$ and $R^7$ are both independently —$CF_3$.

In the compounds of formulae (I) and (II), preferably $R^8$ is hydrogen.

In the compounds of formulae (I) and (II), preferably $R^{11}$ is hydrogen or fluoro.

In the compounds of formulae (I) and (II), preferably $R^{12}$ and $R^{13}$ are both independently hydrogen.

In the compounds of formulae (I) and (II), preferably Z is —$CH_3$.

In the compound of formula (III), preferably, the leaving group LG is chloro.

Suitable bases of use in the above reaction include organic bases or, more preferably, inorganic bases. Suitable organic bases include diisopropylethylamine or triethylamine. Suitable inorganic bases include sodium hydride or potassium carbonate.

Suitable organic solvents of use in the above reaction include diimethylformamide (especially where an inorganic base is used) and acetonitrile (especially where an organic base is used).

Most preferably, the above reaction is effected in, dimethylformamide in the presence of potassium carbonate.

Conveniently, the above reaction is effected at room temperature.

Conveniently, the compound of formula (II), and in particular 2-(R)-(1-(R)-(3,5-bis(trifluoromethyl)phenyl)ethoxy)-3-(S)-(4-fluorophenyl)-morpholine, of use in step (i) of the above reaction is in the form of its free base. Preferably the compound of formula (II), and in particular 2-(R)-(1-(R)-(3,5-bis(trifluoromethyl)phenyl)ethoxy)-3-(S)-(4-fluorophenyl)-morpholine, of use in step (i) of the above reaction is in the form of its (R)-camphor sulfonic acid salt. More preferably, the compound of formula (II), and in particular 2-(R)-(1R)-(3,5-bis-(trifluoromethyl)phenyl)ethoxy)-3-(S)-(4-fluorophenyl)morpholine, of use in step (i) of the above reaction is in the form of its para-toluenesulfonic acid salt.

According to a further or alternative aspect of the present invention, there is provided a process for the preparation of 3-chloromethyl-1,2,4-triazolin-5-one which comprises:

(i) treatment of semicarbazide hydrochloride with benyloxyacetyl chloride under Schotten-Baumann conditions to give benzyloxyacetylsemicarbazide;

(ii) cyclisation of the product of step (i) under basic conditions to give 3-benyloxymethyl-1,2,4-triazolin-5-one;

(iii) hydrogenation of the product of step (ii) to give 3-hydroxymethyl-1,2,4-triazolin-5-one; and (iv) treatment of the product of step (iii) with a chlorinating agent to give 3-chloromethyl-1,2,4-triazolin-5-one.

According to yet a further or alternative aspect of the present invention, there is provided a process for the preparation of 3-hydroxymethyl-1,2,4-triazol-5-one which comprises steps (i) to (iii) as described above.

In step (i) above, the Schotten-Baumann conditions preferably involve use of aqueous alkali in a suitable solvent such as an ether, for example, tetrahydrofuran, at a reduced temperature, for example, between −10° C. and +10° C., preferably 0° C. A particularly suitable aqueous alkali is aqueous sodium hydroxide.

In step (ii) above, cyclisation is preferably effected in the presence of a base such as an alkali metal hydroxide, for example, sodium hydroxide, at an elevated temperature, conveniently at reflux.

In step (iii) above, hydrogenation may be effected by catalytic hydrogenation using hydrogen in a suitable organic solvent such as an alcohol, for example, methanol, in the presence of a noble metal catalyst such as palladium or platinum or an oxide thereof on a support such as charcoal, and conveniently at room temperature and pressure. More preferably, the hydrogenation is effected by transfer hydrogenation in a suitable organic solvent such as an alcohol, for example, methanol, using a hydrogenation catalyst, in particular, palladium on charcoal, in the presence of a hydrogen donor such as sodium hypophosphite, triethylammonium formate, potassium formate, ammonium formate or cyclohexene. Ammonium formate in water is especially preferred. The transfer hydrogenation is preferably effected at an elevated temperature, for example, between 50° C. and 70° C., and preferably between 55° C. and 60° C.

In step (iv) above, the chlorinating agent is, for example, an inorganic, acid chloride such as $SOCl_2$, $PCl_5$, $PCl_3$ and $POCl_3$. Thionyl chloride ($SOCl_2$) is particularly preferred. The reaction is preferably effected in an organic solvent such as acetonitrile, conveniently at room temperature and pressure.

The following non-limiting examples illustrate processes according to the present invention:

EXAMPLE 1

Preparation of 2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl)morpholine A solution of 3-chloromethyl-1,2,4-triazolin-5-one (3.18 g) in DMF (30 ml) was added over 1 hour to a slurry of 2-(R)-(1-(R)-(3,5-bis(trifluoromethyl)phenyl)ethoxy)-3-(S)-(4-fluorophenyl)morpholine (R)-camphor sulfonic acid salt (15 g) and potassium carbonate (7.71 g) in DMF (100 ml) at 22° C. The reaction mixture was aged at 22° C. for 20 minutes, then water (400 ml) was added over 30 minutes. The crystallising mixture was cooled in an ice bath, aged for 30 minutes and the product collected by filtration. The solid title compound was washed with water (400 ml), air dried and dried in vacuo at 45–50° C. Yield=11.4 g; 98.1% HPLC w/w assay; 93.2% assay yield; (97.1A% HPLC profile).

EXAMPLE 2

Steps (i) and (ii) Preparation of 3-benzyloxymethyl-1,2,4-triazolin-5-one

Sodium hydroxide pellets (10.83 g) were added to a cold (0° C.), vigorously stirred, solution of semicarbazide hydrochloride (15.1 g) in water (10 ml)/THF (50 ml) under a nitrogen atmosphere. A solution of benzyloxyacetyl chloride (25 g) in THF (100 ml) was added over five minutes and the mixture aged at 0° C. for 2 hours (reaction complete by HPLC).

THF was removed under reduced pressure, 2M sodium hydroxide (60 ml) was added and the solution heated to reflux temperature for 5 hours. The reaction mixture was cooled to room temperature and left to stand for 18 hours. The solution was neutralised with 6M hydrochloric acid and the slurry cooled in an ice-bath for 1 hour. The product was collected by filtration, washed with cold water (10 ml) and dried in vacuo. 3-Benzyloxy-methyl-1,2,4-triazolin-5-one (16.7 g) was obtained in 60% yield as a white crystalline solid. mp. 190–192° C.; $^1$H NMR in $d_6$ DMSO δ=4.20 (2H, s, PhC$\underline{H}_2$), 4.42 (2H, s, OC$\underline{H}_2$=N), 7.25 (5H, s Ph), 11.34 (1H, s, N$\underline{H}$) and 11.50 (1H, s, N$\underline{H}$) ppm and $^{13}$C NMR in $d_6$ DMSO, δ=64.1 (O$\underline{C}$H$_2$C=N), 72.4 (Ph$\underline{C}$H$_2$O), 128.5 (Ph), 128.6 (Ph), 129.1 (Ph), 138.5 (Ph), 145.4 ($\underline{C}$=N) and 157.1 (NH$\underline{C}$ONH) ppm; mass spectroscopy M+H=206, M+NH$_4$=223.

Step (iii) Preparation of 3-hydroxymethyl-1,2,4-triazolin-5-one

3-Benzyloxymethyl-1,2,4-triazolin-5-one (31 g) and 10% palladium on charcoal (3.1 g) were slurried in methanol (200 ml), under a nitrogen atmosphere. A solution of ammonium formate (47.7 g) in water (20 ml) was added and the mixture was vigorously stirred and heated to 55–60° C. 10% Palladium on charcoal (3.1 g) was added after 2 hours and at 3 hours catalyst (1.55 g) and ammonium formate (9.5 g) in water (4 ml) were charged. After 4 hours the reaction mixture was cooled to room temperature and left to stand overnight. The methanol solution was evaporated, under reduced pressure, to low volume and flushed by continuous addition of methanol (3 L), at 50–55° C., to remove the excesss ammonium formate. The hot mixture was filtered through solka floc (15 g), the filtrate concentrated to low volume and solvent switched to acetonitrile (2×400 ml). The slurry was concentrated to about 100 ml, the product collected by filtration and then dried in vacuo. 3-Hydroxymethyl-1,2,4-triazolin-5-one (17.1 g) was obtained in 98.3% yield mp. 187–189° C. (Lit=187° C.); $^1$H NMR in $d_6$ DMSO δ=4.34 (2H, s, HOC$\underline{H}_2$) and 11.42 (2H, bs N$\underline{H}$) ppm and $^{13}$C NMR in $d_6$ DMSO δ=56.3 (HO$\underline{C}$H$_2$), 148.5 (CH$_2$$\underline{C}$=N) and 157.1 (NH$\underline{C}$ONH) ppm; mass spectroscopy M+H=116. M+NH$_4$=133.

EXAMPLE 3

Preparation of 3-Chloromethyl-1,2,4-triazolin-5-one

Thionyl chloride (19.9 g) was added, over five minutes, to a slurry of 3-hydroxymethyl-1,2,4-triazolin-5-one (17 g) in acetonitrile (170 ml) at 20° C. under a nitrogen atmosphere. The reaction mixture was aged at 20° C. for 18 hours. [Note: after 30 minutes all the starting material had dissolved. At 1 hour the product began to crystallise]. TLC analysis (SiO$_2$; ethyl acetate/methanol (9/1); I$_2$) indicated that the reaction was complete. Hexane (510 ml) was added in one portion, the reaction cooled in an ice bath for 1 hour and the product collected by filtration. The solid was washed with hexane (100 ml) and dried in vacuo. 3-Chloromethyl-1,2,4-triazolin-5-one (17.2 g) was obtained as a white solid in 87.4% yield. mp 197–199° C.; $^1$H NMR in $d_6$ DMSO δ=4.43 (2H, s, C$\underline{H}_2$), 11.48 (1H, s, N$\underline{H}$) and 11.64 (1H, s, N$\underline{H}$) ppm and $^{13}$C NMR in $d_6$ DMSO, δ=37.0 (Cl$\underline{C}$H$_2$), 144.4 (CH$_2$$\underline{C}$=N) and 156.8 (NH$\underline{C}$ONH) ppm.

EXAMPLE 4

Alternative Preparation of 2-(R)-(1-(R)-(3,5-bis(trifluoromethyl)phenyl)-ethoxy)-3-(S)-(4-fluorophenyl)-4-(3-(5-oxo-1H,4H-1,2,4-triazolo)methyl)morpholine (1) Alternative Method using N,N-diisopropylethylamine/DMF A solution of 3-chloromethyl-1,2,4-triazolin-5-one (2.56 g) in DMF (20 ml) was added over 1 hour to a slurry of 2-(R)-(1-(R)-(3,5-bis(trifluoromethyl)phenyl)ethoxy)-3-(S)-(4-fluorophenyl)morpholine para-toluenesulfonic acid salt (12 g) and N,N-diisopropylethylamine (5.15 g) in DMF (40 ml) at 21° C. The reaction was aged at 21–23° C. for 30 minutes, then water (120 ml) was added over 20 minutes. The crystallising mixture was cooled in an ice bath, aged for 30 minutes and the product collected by filtration. The solid title compound was washed water (96 ml), air dried and dried in vacuo at 50° C. Yield=9.65 g; 99.7% isolated yield.

(2) Alternative Method using potassium carbonate/DMF

A solution of 3-chloromethyl-1,2,4-triazolin-5-one (1.40 g) in DMF (13.5 ml) was added over 1 hour to a slurry of 2-(R)-(1-(R)-(3,5-bis(trifluoromethyl)phenyl)ethoxy)-3-(s)-(4-fluorophenyl)morpholine para-toluenesulfonic acid salt (6.77 g) and potassium carbonate (1.55 g) in DMF (27 ml) at 19° C. The reaction was aged at 19–21° C. for 30 minutes, then water (81 ml) was added over 20 minutes. The crystallising mixture was cooled in an ice bath, aged for 30 minutes and the product collected by filtration. The solid title compound was washed with water (54 ml), air dried and dried in vacuo at 50° C. Yield=5.37 g; 98.0% HPLC w/w assay; 96.4% assay yield.

What is claimed is:

1. A process for the preparation of 3-chloromethyl-1,2,4-triazolin-5-one which comprises:
   (i) treatment of semicarbazide hydrochloride with benzyloxyacetyl chloride under Schotten-Baumann conditions to give benzyloxyacetylsemicarbazide;
   (ii) cyclisation of the product of step (i) under basic conditions to give 3-benzyloxymethyl-1,2,4-triazolin-5-one;
   (iii) hydrogenation of the product of step (ii) to give 3-hydroxymethyl-1,2,4-triazolin-5-one; and
   (iv) treatment of the product of step (iii) with a chlorinating agent to give 3-chloromethyl-1,2,4-triazolin-5-one.

2. The process according to claim 1 wherein, in step (i), the Schotten-Baumann conditions involve use of aqueous alkali in an ether, at a reduced temperature.

3. The process according to claim 2 wherein the aqueous alkali is aqueous sodium hydroxide.

4. The process according to claim 3 wherein the ether is tetrahydrofuran.

5. The process according to claim 4 wherein the Schotten Baumann reaction is effected between −10° C. and +10° C.

6. The process according to claim 1 wherein, in step (ii), cyclisation is effected in the presence of a base at an elevated temperature.

7. The process according to claim 6 wherein the base is an alkali metal hydroxide.

8. The process according to claim 7 wherein the alkali metal hydroxide is sodium hydroxide.

9. The process according to claim 6 wherein the reaction is effected at reflux.

10. The process according to claim 1 wherein, in step (iii), hydrogenation is effected by catalytic hydrogenation using hydrogen in an organic solvent, and in the presence of a noble metal catalyst on a support.

11. The process according to claim 10 wherein the organic solvent is an alcohol.

12. The process according to claim 11 wherein the alcohol is methanol.

13. The process according to claim 10 wherein the noble metal catalyst is palladium or platinum or an oxide thereof.

14. The process according to any one of claims 10 wherein the support is charcoal.

15. The process according to any one of claim 10 wherein the reaction is effected at room temperature and pressure.

16. The process according to claim 1 wherein, in step (iii), hydrogenation is effected by transfer hydrogenation in a organic solvent using a hydrogenation catalyst in the presence of a hydrogen donor.

17. The process according to claim 16 wherein the organic solvent is an alcohol.

18. The process according to claim 17 wherein the alcohol is methanol.

19. The process according to claim 16 wherein the hydrogenation catalyst is palladium on charcoal.

20. The process according to claim 16 wherein the hydrogen donor is selected from sodium hypophosphite, triethylammonium formate, potassium formate, ammonium formate and cyclohexene.

21. The process according to claim 20 wherein the hydrogen donor is ammonium formate in water.

22. The process according to claim 21 wherein the transfer hydrogenation is effected at an elevated temperature.

23. The process according to claim 22 wherein the reaction is effected at a temperature between 50° C. and 70° C.

24. The process according to claim 1 wherein, in step (iv), the chlorinating agent is an inorganic acid chloride.

25. The process according to claim 24 wherein the inorganic acid chloride is selected from $SOCl_2$, $PCl_5$, $PCl_3$, and $POCl_3$.

26. The process according to claim 24 wherein the reaction is effected in an organic solvent.

27. The process according to claim 26 wherein the organic solvent is acetonitrile.

28. The process according to claim 24 wherein the reaction is effected at room temperature and pressure.

29. A compound which is 3-chloromethyl-1,2,4-triazolin-5-one.

* * * * *